US012343552B2

(12) United States Patent
Velasco Valcke

(10) Patent No.: US 12,343,552 B2
(45) Date of Patent: Jul. 1, 2025

(54) APPLICATION OF JERK ELECTROMAGNETIC FIELDS FOR MATERIAL AND TISSUE STIMULATION

(71) Applicant: PANACEA QUANTUM LEAP TECHNOLOGY LLC, Dallas, TX (US)

(72) Inventor: Francisco Javier Velasco Valcke, Bogotá (CO)

(73) Assignee: Panacea Quantum Leap Technology LLC, Dallas, TX (US)

( * ) Notice: Subject to any disclaimer, the term of this patent is extended or adjusted under 35 U.S.C. 154(b) by 1132 days.

(21) Appl. No.: 17/259,212

(22) PCT Filed: Jul. 16, 2019

(86) PCT No.: PCT/US2019/042081
§ 371 (c)(1),
(2) Date: Jan. 11, 2021

(87) PCT Pub. No.: WO2020/018594
PCT Pub. Date: Jan. 23, 2020

(65) Prior Publication Data
US 2021/0268298 A1    Sep. 2, 2021

(30) Foreign Application Priority Data
Jul. 16, 2018   (CO) .............. 2018/0007468

(51) Int. Cl.
*A61N 2/02*       (2006.01)
*A61N 1/08*       (2006.01)
(Continued)

(52) U.S. Cl.
CPC .............. *A61N 2/02* (2013.01); *A61N 1/08* (2013.01); *A61N 1/10* (2013.01); *A61N 1/36002* (2017.08);
(Continued)

(58) Field of Classification Search
CPC ........ A61N 1/36002; A61N 1/08; A61N 1/10; A61N 1/40; A61N 2/00; A61N 2/002;
(Continued)

(56) References Cited

U.S. PATENT DOCUMENTS 8,137,259 B1    3/2012  Dennis et al.
2002/0165583 A1  11/2002  Tepper et al.
(Continued)

FOREIGN PATENT DOCUMENTS

WO   2012012159 A1   1/2012
WO   2012045079 A2   4/2012
(Continued)

OTHER PUBLICATIONS

Xu, X.-X et al., "New Concepts in Electromagnetic Jerky Dynamics and Their Applications in Transient Processes of Electric Circuit," Progress In Electromagnetics Research M, vol. 8, 181-194, 2009, (online) (retrieved on Feb. 6, 2020 (Feb. 6, 2020)) Retrieved from the Internet <URL: http://www.jpier.org/PIERM/pier.php?paper=09021501>.
(Continued)

*Primary Examiner* — Carrie R Dorna
(74) *Attorney, Agent, or Firm* — Maine Cernota & Curran

(57) ABSTRACT

The present disclosure relates to methods and devices for applying electromagnetic field jerk to materials and tissues. A first method comprises the following steps: A) generating an activation signal having a waveform that generates electromagnetic field jerk; and B) applying the activation signal to the arrangement of electromagnetic transducers.
A second method comprises the following steps: a) generating a carrier signal with a series of pulses by a computing unit; b) generating a modulating signal that generates jerk; c) generating an activation signal that modulates the carrier signal using the modulating signal that generates jerk; d) applying the activation signal to the arrangement of electromagnetic transducers.
(Continued)

Some embodiments of the disclosed methods and devices are used for fracturing, pulverizing and reducing particle size of material and tissues.

30 Claims, 10 Drawing Sheets

(51) Int. Cl.
    *A61N 1/10*     (2006.01)
    *A61N 1/36*     (2006.01)
    *A61N 1/40*     (2006.01)
    *A61N 2/00*     (2006.01)

(52) U.S. Cl.
    CPC ............... *A61N 1/40* (2013.01); *A61N 2/002* (2013.01); *A61N 2/004* (2013.01)

(58) Field of Classification Search
    CPC ........ A61N 2/004; A61N 2/005; A61N 2/008; A61N 2/02

See application file for complete search history.

(56) References Cited

U.S. PATENT DOCUMENTS

| | | |
|---|---|---|
| 2011/0046687 A1 | 2/2011 | Naschberger |
| 2012/0226200 A1 | 9/2012 | Wagner et al. |
| 2015/0157873 A1 | 6/2015 | Sokolowski |
| 2018/0036531 A1 | 2/2018 | Schwarz et al. |

FOREIGN PATENT DOCUMENTS

| | | |
|---|---|---|
| WO | 2012056027 A1 | 5/2012 |
| WO | 2016134367 A1 | 8/2016 |
| WO | WO-2019/155405 A2 | 8/2019 |
| WO | WO-2019/155407 A2 | 8/2019 |

OTHER PUBLICATIONS

International Search Report / Written Opinion mailed Feb. 25, 2020 for PCT/US2019/042081.

Amelia Carolina Sparavigna, Jerk and Hyperjerk in a Rotating Frame of Reference, Article, 2015, 29-33, vol. 4, Issue 03, International Journal of Sciences, Manchester, England.

R.C. Zowarka; J.P. Kajs, Electromagnetic force, jerk, and electric gun projectiles, Article, Jan. 1993, 895-900, vol. 29, issue 1, IEEE Transactions on Magnetics.

Office Action translation for Foreign Application No. NC2021/0001840 mail date Mar. 11, 2025, 16 pages.

APPLICATION OF JERK ELECTROMAGNETIC FIELDS FOR MATERIAL AND TISSUE STIMULATION

CROSS-REFERENCE TO RELATED APPLICATION

This application is the National Stage of International Application No. PCT/US2019/042081, filed Jul. 16, 2019, and claims the priority benefit of Colombia application serial no. NC2018/0007468 filed on 16 Jul. 2018. The entirety of each of the above-mentioned patent applications is hereby incorporated by reference herein and made a part of this application.

BACKGROUND

Technical Field

This disclosure is generally related to methods for tissue or material stimulation with electromagnetic fields. More specifically, it relates to a method for tissue or material stimulation using jerk-generating electromagnetic fields, for example, electrostatic fields, electrical fields and magnetic fields that generate jerk. Jerk is generally described in https://en.wikipedia.org/wiki/Jerk (physics).

Description of Related Art

The jerk effect has typically been studied within the context of acceleration in mechanical and transport engineering (e.g. robot arms, automobile brake systems) (https://arxiv.org/ftp/arxiv/papers/1503/1503.07051.pdf), electromagnetic jerky dynamics and their applications in transient processes of electric circuits (http://www.jpier.org/PIERM/pierm08/15.09021501.pdf) and electric gun projectiles (https://ieeexplore.ieee.org/document/195695.

SUMMARY

This disclosure refers to methods and devices for stimulating tissue or materials by electromagnetic transducers using jerk-generating electromagnetic fields, for example: electrostatic fields, electrical fields and magnetic fields that generate jerk, which have an activation signal applied to an arrangement of electromagnetic transducers. A drastic variation of the electromagnetic field vector, electrostatic field, electrical field and magnetic field in the tissue of interest or material is obtained. Said drastic variation generates an over-acceleration of the cells comprising said tissue or the particles of the material. This over-acceleration is known in physics as jerk, see also, e.g., https://en.wikipedia.org/wiki/Jerk (physics).

The first method for stimulating a tissue by an arrangement of electromagnetic transducers, comprises the following steps: A) generating an activation signal having a waveform that generates electromagnetic field jerk by a computing unit; and B) applying the activation signal to the arrangement of electromagnetic transducers by the computing unit; wherein the arrangement of electromagnetic transducers produces jerk-generating electromagnetic fields which mechanically stimulate the tissue upon application of the activation signal.

The activation signal having a waveform that generates electromagnetic field jerk, for example, has a frequency between 1 Hz (hertz) and 3 MHZ (megahertz), optionally between 1 Hz (hertz) and 500 kHz (kilohertz).

Said activation signal is selected between an alternating current or a direct current signal, pulsed signal, square wave signal with duty cycle variation, triangular wave signal, sawtooth wave signal, segmented signal, or combinations thereof. For example, it may be a pulsed signal with pulse durations between about 1 ns and 0.5 s.

In one embodiment of the disclosure, the activation signal has a voltage range between −20 kV (kilovolts) and 20 kV (kilovolts) depending on whether the arrangement of electromagnetic transducers are in contact or not with the tissue or material of interest.

The second method for stimulating a tissue or material by an arrangement of electromagnetic transducers comprises the following steps: a) generating a carrier signal with a series of pulses by means of a signal generator; b) generating a modulating signal which generates jerk by means of a signal generator; c) generating an activation signal modulating the carrier signal with the modulating signal that generates jerk; d) applying the activation signal to the arrangement of electromagnetic transducers by a computing unit; wherein the arrangement of electromagnetic transducers produces jerk-generating electromagnetic fields which mechanically stimulate the tissue or material upon application of the activation signal.

In one embodiment of the disclosed method, the frequency of the carrier signal is between 1 Hz (hertz) and 3 MHz (megahertz), optionally between 1 Hz (hertz) and 500 kHz (kilohertz).

On the other hand, the modulating signal generated by jerk has a frequency between 0.1 Hz (hertz) and 5 kHz (kilohertz), optionally between 0.1 Hz (hertz) and 10 Hz (hertz).

In some embodiments of the disclosed method, the duration of each pulse duration of the carrier signal is between 1 ns and 0.5 s.

In addition, this disclosure includes using jerk.generating electromagnetic fields in order to reduce the particle size of a material.

The disclosure also includes a device for stimulating a tissue with electromagnetic fields, the device comprising: a computing unit; an external power source connected to the computing unit; a decoupling circuit connected to the external power source and to the computing unit; an arrangement of electromagnetic transducers connected to the computing unit and to the decoupling circuit; wherein the computing unit implements a method to generate an activation signals that receive the arrangement of electromagnetic transducers through the decoupling circuit.

Not only does the device allow jerk-generating electromagnetic fields to be applied to tissues, it also allows the reduction of the particle size of suspended dead cells in the tissue, for example in an in vivo environment in order to improve and accelerate the elimination of said suspended dead cells through the lymphatic system of a living organism.

DETAILED DESCRIPTION

The disclosure relates to a method for stimulating a tissue or material by applying a jerk-generating electromagnetic field via an arrangement of electromagnetic transducers.

Figure 10:
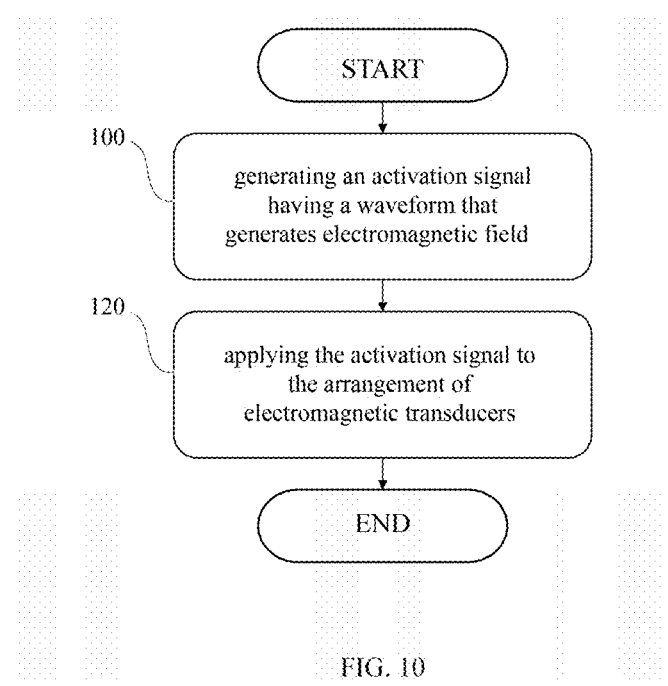
FIG. 10 shows an example of a flowchart of the method for stimulating a tissue using an arrangement of electromagnetic transducers of this disclosure.

FIG. 10 shows an example of a flowchart of the method for stimulating a tissue using an arrangement of electromagnetic transducers of this disclosure, the method comprising the following steps: (100) generating an activation signal having a waveform that generates electromagnetic field jerk by a computing unit; and (120) applying the activation signal to the arrangement of electromagnetic transducers by the computing unit; wherein the arrangement of electromagnetic transducers produces jerk-generating electromagnetic fields which mechanically stimulate the tissue upon application of the activation signal to the electromagnetic transducers by the computing unit.

In this disclosure, the expression "mechanically stimulating the tissue" corresponds to applying an electromagnetic force to the tissue or to the material sufficient enough to physically move, deform, compress, expand, divide, shear or fracture said tissue or material. It should be understood that the applied electromagnetic field affects the behavior of charged elements in the vicinity of the field. A hammering, shearing or distortion effect is achieved when the electromagnetic force applied to the tissue or material is strong enough to generate mechanical stress surpassing the normal strain zone of the tissue or the particles of material, thus resulting in the moving, deforming, compressing, expanding, dividing, shearing or fracturing of the tissue cells or particles of a material.

The activation signal is a signal which abruptly changes its parameters, for example: polarity, slope, or voltage value in a certain fraction of time. For example, a signal changing from −20 kV to 20 kV in a time period ranging between about 1 ns and 0.5 s.

Optionally, the fraction of time the activation signal takes for abruptly changing the parameters of the electromagnetic field vector is selected from about 1 ns to about 0.5 s, from about 1 ns to about 49 µs, from about 10 ns to about 100 ns, from about 20 ns to about 100 ns, from about 30 ns to about 100 ns, from about 40 ns to about 100 ns, from about 50 ns to about 100 ns, from about 60 ns to about 100 ns, from about 70 ns to about 100 ns, from about 80 ns to about 100 ns, from about 90 ns to about 100 ns, from about 10 ns to about 20 ns, from about 20 ns to about 30 ns, from about 30 ns to about 40 ns, from about 40 ns to about 50 ns, from about 50 ns to about 60 ns, from about 60 ns to about 70 ns, from about 70 ns to about 80 ns, from about 80 ns to about 90 ns, from about 90 ns to about 100 ns, from about 100 ns to about 900 ns, from about 200 ns to about 800 ns, from about 300 ns to about 700 ns, from about 400 ns to about 600 ns, from about 100 ns to about 1000 ns, from about 200 ns to about 1000 ns, from about 300 ns to about 1000 ns, from about 400 ns to about 1000 ns, from about 500 ns to about 1000 ns, from about 600 ns to about 1000 ns, from about 700 ns to about 1000 ns, from about 800 ns to about 1000 ns, from about 900 ns to about 1000 ns, from about 100 µs to about 200 µs, from about 200 µs to about 300 µs, from about 300 µs to about 400 µs, from about 400 µs to about 500 µs, from about 500 µs to about 600 µs, from about 600 µs to about 700 µs, from about 700 µs to about 800 µs, from about 800 µs to about 900 µs, from about 900 µs to about 1000 µs, from about 100 µs to about 1000 µs, from about 200 µs to about 1000 µs, from about 300 µs to about 1000 µs, from about 400 µs to about 1000 µs, from about 500 µs to about 1000 µs, from about 600 µs to about 1000 µs, from about 700 µs to about 1000 µs, from about 800 µs to about 1000 µs, from about 900 µs to about 1000 µs, from about 100 ms to about 200 ms, from about 200 ms to about 300 ms, from about 300 ms to about 400 ms, from about 400 ms to about 500 ms, from about 100 ms to about 500 ms, from about 200 ms to about 500 ms, from about 300 ms to about 500 ms, from about 400 ms to about 500 ms.

Figure 1A:
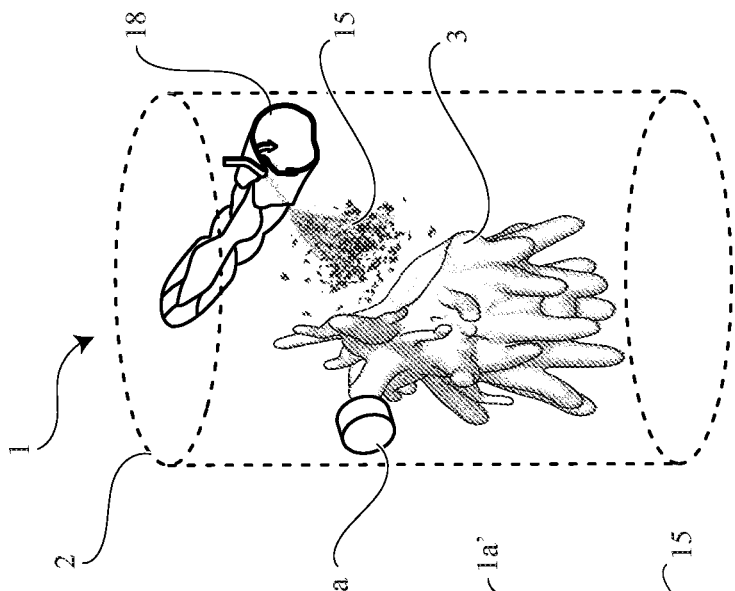
FIG. 1A shows an example of a transducer arrangement covering a volume containing a cancerous tissue that has been previously treated and where a section of the tissue has necrotized.
Figure 1B:
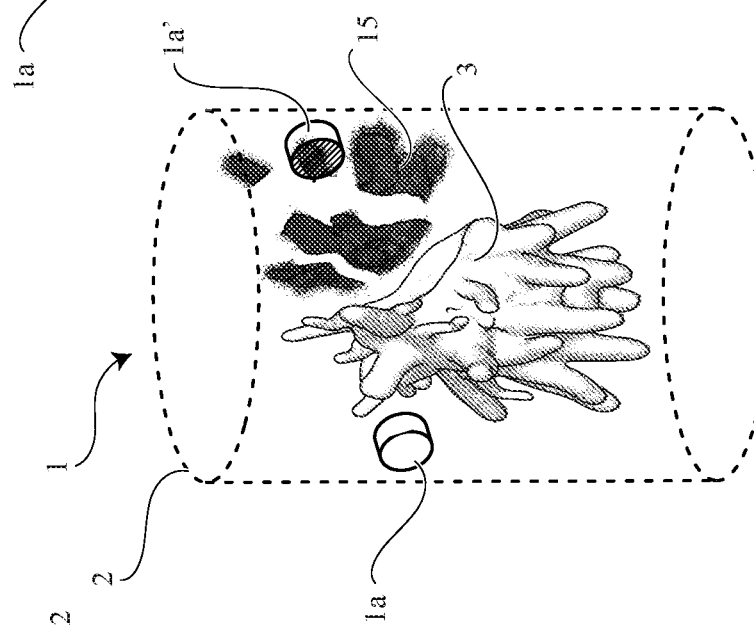
FIG. 1B shows a jerk-generating electromagnetic field applied to the volume via the transducer arrangement, which acts over the necrotized cancer tissue, pulverizing it into smaller particulate matter.
Figure 1C:
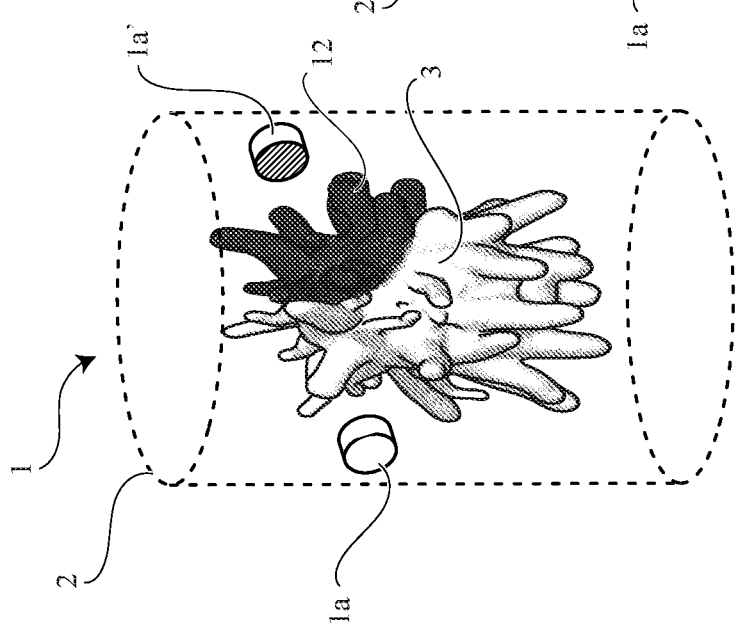
FIG. 1C shows how a similar jerk-generating electromagnetic field applied over the volume also serves to pump the smaller particulate matter suspended in the interstitial fluid into the lymphatic vessels.

The disclosed methods can be used for reducing particle size of a material. The material can be any type of material, including organic, or inorganic, in a solid state or in suspension in a fluid (liquid or gas The disclosed methods can also be used for pulverizing tissue. Making reference to FIG. 1A, when a cancerous tissue (3) is stimulated for a certain time using electromagnetic field treatments, such as the one disclosed in PCT/IB2019/051007, filed on 7 Feb. 2019, some of the resulting dead cancerous cells will start to form a layer or section of necrotic tissue (12). This necrotic tissue (12) starts to present electromagnetic shield that reduces the efficacy of the treatment being applied due to changes in impedance, conductivity and permeability. As shown in FIGS. 1B and 1C, applying the disclosed jerk-generating electromagnetic fields via transducer arrangement (1) (transducers 1a and 1a') allows one to fracture pulverize this necrotic tissue (12) into finer particulate matter (15). This reduces the electromagnetic shield effect mentioned above, and in turn also facilitates the elimination of the necrotic tissue through the lymphatic vessels (18). Furthermore, by applying a different jerk-generating electromagnetic field, one can also generate a pumping effect over the particulate matter (15) suspended in the interstitial fluid so as to accelerate the evacuation into the lymphatic vessels (18).

FIG. 1B shows an arrangement of electromagnetic transducers (1), consisting of a transducer (1a) and a transducer (1a'), on the surface of a volume (2).

Figure 8:
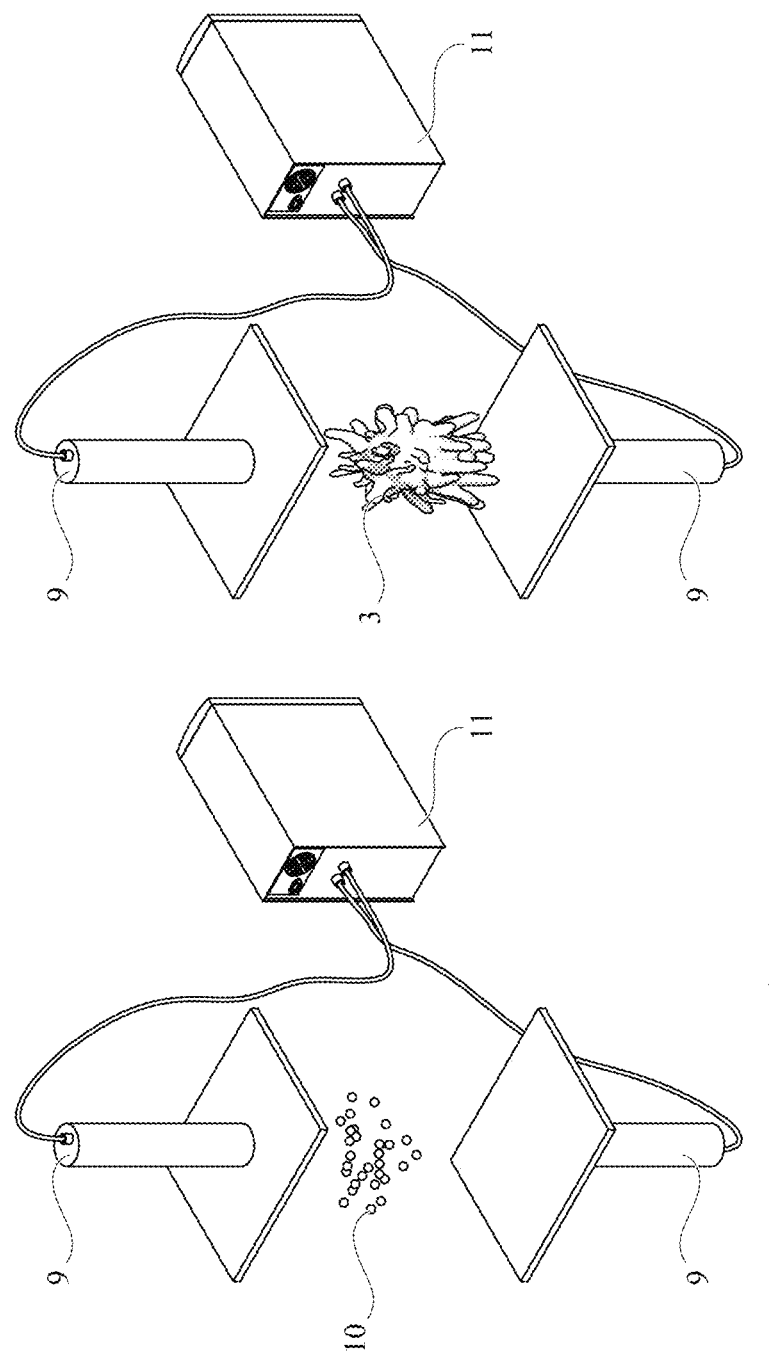
FIG. 8 shows an example of a parallel plate electrode configuration.

As shown in FIGS. 8A and 8B, in one embodiment of the disclosure, the active face of the transducer is covered by a dielectric material (17) allowing electrical isolation of the electromagnetic transducer from the tissue (3) or material (10) of interest. Moreover, the active face can have different shapes, which are selected from the group of geometric figures such as squares, rectangles, circles, ovals, concentric rings, or combinations thereof.

According to the present disclosure, an electromagnetic transducer is a device capable of transforming or converting a certain electrical energy signal (e.g., an activation signal) into electromagnetic energy expressed by intensities of the electrical field, electrostatic field and magnetic field.

For purposes of this document, electromagnetic transducers shall be understood as electromagnetic field transducers, which may be electric field transducers, magnetic field transducers, electrostatic field transducers, or combinations thereof.

It should be noted when referring to electromagnetic phenomenon where the electric field prevails, electromagnetic transducers are to be understood as electric field transducers. When the electromagnetic phenomenon that prevails is the magnetic field, it will be understood that electromagnetic transducers are magnetic field transducers. When the electromagnetic phenomenon that prevails is the electrostatic field, it will be understood that electromagnetic transducers are electrostatic field transducers.

In some embodiments of the disclosure, the electromagnetic transducers of the arrangement of electromagnetic transducers are selected from electric field transducers and magnetic field transducers, electrostatic field transducers, or combinations thereof.

Furthermore, in other embodiments of the disclosure, electric field transducers and electrostatic field transducers are selected, among others, from the group consisting of motors, electrodes, photoelectric transducers, electric induction actuators, conductive plates which generate electric field, antennas, or combinations thereof. On the other hand, the magnetic field transducers are selected, among others, from the group consisting of motors, magnetic induction actuators, core or non-core coils that generate magnetic fields, electromagnets, antennas, or combinations thereof.

In an example of the present disclosure, the active face of the electric field transducers in the arrangement of electromagnetic transducers (1) is in contact with the tissue (3) outer surface (typically, the skin of the subject whose tissue is being stimulated). In this way, less electric potential is required for the operation of the electric field transducers, in comparison with another alternative where the electric field transducers are at a certain distance from the tissue (3) outer surface.

In another example, the active face of the transducers forming the arrangement of electromagnetic transducers (1) is spaced at a certain distance from the tissue (3) outer surface (necessary, for example, when it is not possible to reach physical contact with the tissue (3) outer surface). In this way, greater electric potential is required for the operation of the electric field transducers in comparison with the alternative where the electric field transducers are in contact with the tissue (3) outer surface.

For this disclosure the term tissue refers to the biological tissues of living beings comprised of one or more cells, may be constituted by cells of only one class, all the same, or by various types of cells arranged in an orderly fashion to form an organ or an organism. The cited tissue may be healthy tissue, such as epithelial tissue, connective tissue, muscle tissue, muscular package, nerve tissue, or combinations thereof. The tissue may also be a tissue with a total or partial bio-chemical imbalance in healthy tissue, said bio-chemical imbalance in turn may correspond to benign tissue, neoplastic tissue, malignant neoplastic tissue or any cell out of homeostasis or in homeostasis. Also, tissue may refer to cells in vivo or prior to implantation said cells into an in vivo environment. Tissue may also refer to cells in an ex vivo environment. Tissue may also refer to necrotic tissue.

For this disclosure, tissue impedance response is the measurement of the voltage drop in the electromagnetic transducers applied signal when stimulating the tissue (3). In other words, as the voltage applied to the tissue varies over time according to tissue electromagnetic stimulation, the tissue impedance response varies over time in voltage. Tissue impedance also behaves as described in application no. PCT/IB2019/051007, filed on 7 Feb. 2019.

FIG. 8A shows an arrangement of electromagnetic transducers (1) in a configuration with a pair of parallel plate electrodes (9), the active faces of said electrodes are facing each other and in the direction of a material (10). Each electrode of said pair is connected to a tissue stimulating device (11) executing the disclosed method to generate an activation signal with generating electromagnetic fields that generate jerk and allowing to reduce the particle size of the material (10). In one example, said activation signal is a pulsed signal changing between −20 kV and 20 kV at a time between 1 ns and 0.5 s and with a frequency between 1 Hz (hertz) and 3 MHz (megahertz), optionally between 1 Hz (hertz) and 500 kHz (kilohertz).

FIG. 8B teaches a specific configuration of electromagnetic transducers similar to the one of FIG. 8A and as also illustrated in FIG. 1B. However, the active faces of said pair of transducers are in the direction of a tissue (3) and the jerk-generating electromagnetic fields allow the tissue (3) to be mechanically stimulated. In one example, said activation signal is a pulsed signal that changes between −20 kV and 20 kV at a time between 1 ns and 0.5 s and with a frequency between 1 Hz (hertz) and 3 MHz (megahertz), optionally between 1 Hz (hertz) and 500 kHz (kilohertz).

Figure 9:
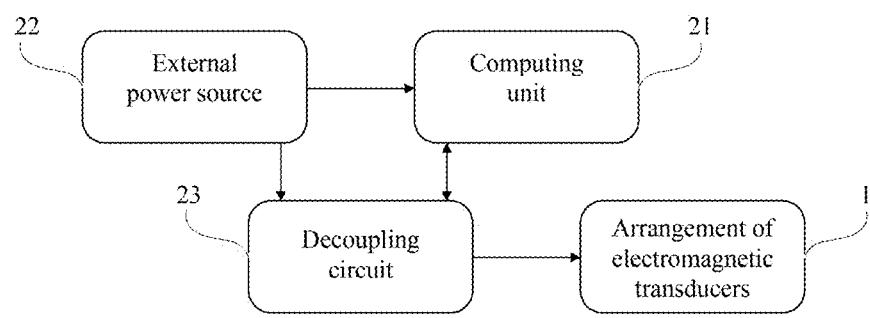
FIG. 9 shows a block diagram of an example of a tissue stimulating device of this disclosure.

FIG. 9 is an example of a tissue stimulating device (11) of the present disclosure. The tissue stimulating device (11) comprises a computing unit (21), an external power source (22) connected to the computing unit (21), a decoupling circuit (23) connected to the external power source (22) and to the computing unit (21), an arrangement of electromagnetic transducers (1) connected to the decoupling circuit (23). The computing unit (21) implements the methods of the disclosure (method for stimulating a tissue by an arrangement of electromagnetic transducers using jerk-generating electromagnetic fields) and may be configured with the tissue stimulating device in order to generate the activation signals receiving the jerk-generating electromagnetic field, electrostatic field, electric field, and magnetic field transducers or combination thereof, by a decoupling circuit (23).

Alternatively, in one example of the tissue stimulating device (11) of this disclosure, the arrangement of electromagnetic transducers (1) is connected to the computing unit (21) directly.

Optionally, the parameters of each activation signal such as frequency, phase, amplitude, duty cycle, can be modified by instructions of a remote computing unit, by a user through an HID connected to the tissue stimulating device.

The computing unit (21) receives a tissue impedance response feedback and the activation signals are dynamically adjusted for the transducers that stimulate the tissue in relation to the tissue impedance response. In a particular embodiment, the computing unit is a signal generator. This tissue impedance response feedback is a mechanism by which a certain portion of the control the tissue stimulating device (11) is redirected to the input thereof, in order to control its behavior. For example, by stimulating a tissue with electric fields, electrostatic fields, magnetic fields, or combinations thereof, the tissue impedance response may vary. For example, in a particular embodiment of the disclosure, the electric field transducers of an arrangement of electromagnetic transducers are used to measure how the tissue impedance response varies, and said feedback allows dynamically adjusting the activation signal of the transducers. This allows, for example, protecting tissue from overstimulation.

Alternatively, the feedback is not limited to obtaining a measurement of tissue impedance or a tissue impedance response variation to an electromagnetic stimulus of tissue (3). It may also incorporate, for example, a tissue temperature measurement to determine tissue fatigue, taking images of the tissue (3) surface to determine tissue (3) vascularization, or combinations thereof.

In an example of the present disclosure, the activation signal changes its parameters of: voltage amplitude, frequency and phase, pulse duration, duty cycle or pulse position, based on a tissue temperature feedback.

In another example of the present disclosure, the activation signal changes its parameters of: voltage amplitude, frequency, phase, pulse duration, duty cycle or pulse position, based on a tissue impedance response feedback.

A computing unit is understood as a device that processes data, for example, microcontrollers, microprocessors, DSCs (Digital Signal Controller), FPGAs (Field Programmable Gate Array), CPLDs (Complex Programmable Logic Device), ASICs (Application Specific Integrated Circuits), SoCs (System on Chip), PSoCs (Programmable System on Chip), computers, servers, tablets, cellphones, smartphones, signal generators and computer units known to any normally skilled person in the art, or combinations thereof. This computing unit may include a storage device, display device and/or a Human Interface Device (HID), image acquisition device, may be or include a special purpose computing unit programmed to run the method of this disclosure.

A storage device includes, without limiting, RAM memory (cache memory, SRAM, DRAM, DDR), ROM memory (Flash, cache, HDD, SSD, EPROM, EEPROM, removable memory ROM (SD (miniSD, microSD, etc), MMC (MultiMedia Card), Compact Flash, SMC (Smart Media Card), SDC (Secure Digital Card), MS (Memory Stick), among others)), CD-ROM, Digital Versatile Disc (DVD) or other optical storage, magnetic cassettes, magnetic tapes, storage or any other means that can be used to store information and which can be accessed by a computer unit, among others known to those skilled in the art, or combinations thereof. The storage device may have memory registers, in which instructions, data structures and software modules stored.

A display includes, without limitation, monitors capable of being connected to a computing unit and displaying its output. CRT monitor, flat panel display, Liquid Crystal D Liquid Crystal Display (LCD), active matrix LCD, passive matrix LCD, LED displays, display projectors, TV (4KTV, HDTV, Plasma TV, Smart TV), OLED displays, AMOLED Displays, Quantum dot (QD) displays, segments displays, among other devices capable of showing data to a user, known to those skilled in the art, or combinations thereof.

A HID includes, without limiting, keyboard, mouse, trackball, touchpad, pointing stick, joystick, touch screen, among other devices capable of allowing a user to input data into the computing unit of the tissue stimulating device, known to those skilled in the art, or combinations thereof.

The decoupling circuit makes it possible to electrically decouple the external power source from the arrangement of electromagnetic transducers, said circuit may be based on optocouplers, relays, operational amplifiers, resistors, condensers, transformers, diodes and combination of these and other electronic elements for electrically decoupling two electrical circuits or elements.

The external power source makes it possible to provide the electric power required for operation of the arrangement of electromagnetic transducers and may be a device capable of maintaining a power differential between two or more terminals such as an alternating current power source, a continuous current power source, batteries, photovoltaic power source, thermoelectric power source, among other devices capable of maintaining a voltage between two or more terminals known to those skilled in the art, or combinations thereof.

Additionally, the computing unit allows for one or several activation signals to be applied sequentially to each transducer in a certain time, in phase shift with respect to another activation signal or several stimulation signals, randomly or obeying a set program for each of the transducers. These signals are generated by a computing unit or by a signals generator, or combinations thereof, according to programs and feedback.

The programs referred to by the present disclosure correspond to information coded or not in a computing unit and which modifies all parameters of the activation signal that activates the transducers of the arrangement of electromagnetic transducers (1). The parameters of the activation signal are selected among frequency, phase voltage amplitude, pulse duration, duty cycle or pulse position.

An image acquisition device has sensors sensitive to the visible spectrum or to other portions of the electromagnetic spectrum, used to capture an image that is in a visual field of the same. The image acquisition device is selected from the group consisting of compact cameras, APS cameras (Advanced Photo System), SLR cameras SLR (Single Lens Reflex), digital cameras, camera TLR (Twin Lens Reflex), infrared cameras, thermal cameras, scanners and combinations of these.

The sensor element technology of the cameras is selected from the group consisting of CCD (Charge Coupled Device), CMOS (Complementary Metal Oxide Semiconductor) or hybrid CCD/CMOS sensors. Sensor element technology can be selected from the group consisting of color, monochromatic, high definition, high sensitivity, high speed, infrared, infrared of the refrigerated or infrared type of the non-refrigerated type.

Returning to FIG. 10, in step (100), the generation of an activation signal having a waveform that generates electromagnetic field jerk is performed by a computing unit. Said activation signal abruptly changes polarity, slope, or voltage value in a fraction of time determined at least once in a period of the activation signal A waveform that generates jerk generally refers to a waveform described by a mathematical function wherein at least a unit triplet is obtained in its third derivative at some point of the mathematical function. According to the present disclosure, a unit triplet is the second derivative of a Dirac delta function or unit impulse, while a unit doublet is the derivative of a Dirac delta function or unit impulse.

In one example, the activation signal is selected between an alternating current or direct current signal, pulsed signal, squared wave signal with duty cycle variation, sawtooth wave signal, segmented signal, or combinations thereof. Also, for example, the activation signal may be selected from a jerk-generating signal of alternating pulses or non-alternating pulses. The activation signal has a range of voltage amplitude between −20 kV (kilovolts) and 20 kV (kilovolts). By using said ranges of voltage, it is possible to obtain an intensity of the electric field in the tissue (3) between 2 V/cm and 5 V/cm when the active face of the electromagnetic transducers is in contact with the tissue (3) outer surface (again, typically the skin of the subject).

On the other hand, if the electric field transducers are at a defined distance from the tissue (3) outer surface, then the electric field intensity value is between −20 kV/cm and 20 kV/cm for distances between 0.01 cm and 50 cm from the tissue (3) outer surface, and optionally between 0.01 cm and 4 cm from the tissue (3) surface. The latter is to ensure that the intensity of the electric field in the tissue is between 2 V/cm and 5 V/cm.

On the other hand, if tissue stimulation is performed with magnetic field transducers with an activation signal having a voltage amplitude between −20 kV (kilovolts) and 20 kV (kilovolts), it is possible to obtain a magnetic field strength between 0.1 mT (militeslas) equivalent to 1 Gauss and 200 mT (militeslas) equivalent to 2000 Gauss.

In an example of the disclosed method, an activation signal with a maximum electrical voltage of 80 V applied to electric field transducers of the arrangement of electromagnetic transducers (1), with a distance between electrodes of 27 cm is used. This allows obtaining electrical field intensity between 3 V/cm and 5 V/cm in order to stimulate the tissue (3).

Moreover, in another particular example of the disclosed method, it is possible to operate at 120 V for the activation signal when the distance between electrodes is 40 cm. Said electrical voltages are applied to electrodes isolated from the tissue (3) outer surface.

In another different embodiment, the activation signal is a series of pulses with a frequency between 1 Hz (hertz) and 3 MHZ (megahertz), and optionally between 1 Hz (hertz) and 500 kHz (kilohertz).

In turn, the series of pulses of the activation signal has at least one pulse with a duration between 1 ns and 0.5 s.

Optionally, the duration of the pulses of the activation signal can be selected from about 1 ns to about 0.5 s, from about 10 ns to about 100 ns, from about 20 ns to about 100 ns, from about 30 ns to about 100 ns, from about 40 ns to about 100 ns, from about 50 ns to about 100 ns, from about 60 ns to about 100 ns, from about 70 ns to about 100 ns, from about 80 ns to about 100 ns, from about 90 ns to about 100 ns, from about 10 ns to about 20 ns, from about 20 ns to about 30 ns, from about 30 ns to about 40 ns, from about 40 ns to about 50 ns, from about 50 ns to about 60 ns, from about 60 ns to about 70 ns, from about 70 ns to about 80 ns, from about 80 ns to about 90 ns, from about 90 ns to about 100 ns, from about 100 ns to about 900 ns, from about 200 ns to about 800 ns, from about 300 ns to about 700 ns, from about 400 ns to about 600 ns, from about 100 ns to about 1000 ns, from about 200 ns to about 1000 ns, from about 300 ns to about 1000 ns, from about 400 ns to about 1000 ns, from about 500 ns to about 1000 ns, from about 600 ns to about 1000 ns, from about 700 ns to about 1000 ns, from about 800 ns to about 1000 ns, from about 900 ns to about 1000 ns, from about 100 μs to about 200 μs, from about 200 μs to about 300 μs, from about 300 μs to about 400 μs, from about 400 μs to about 500 μs, from about 500 μs to about 600 μs, from about 600 μs to about 700 μs, from about 700 μs to about 800 μs, from about 800 μs to about 900 μs, from about 900 μs to about 1000 μs, from about 100 μs to about 1000 μs, from about 200 μs to about 1000 μs, from about 300 μs to about 1000 μs, from about 400 μs to about 1000 μs, from about 500 μs to about 1000 μs, from about 600 μs to about 1000 μs, from about 700 μs to about 1000 μs, from about 800 μs to about 1000 μs, from about 900 μs to about 1000 μs, from about 100 ms to about 200 ms, from about 200 ms to about 300 ms, from about 300 ms to about 400 ms, from about 400 ms to about 500 ms, from about 100 ms to about 500 ms, from about 200 ms to about 500 ms, from about 300 ms to about 500 ms, from about 400 ms to about 500 ms.

Figure 7:
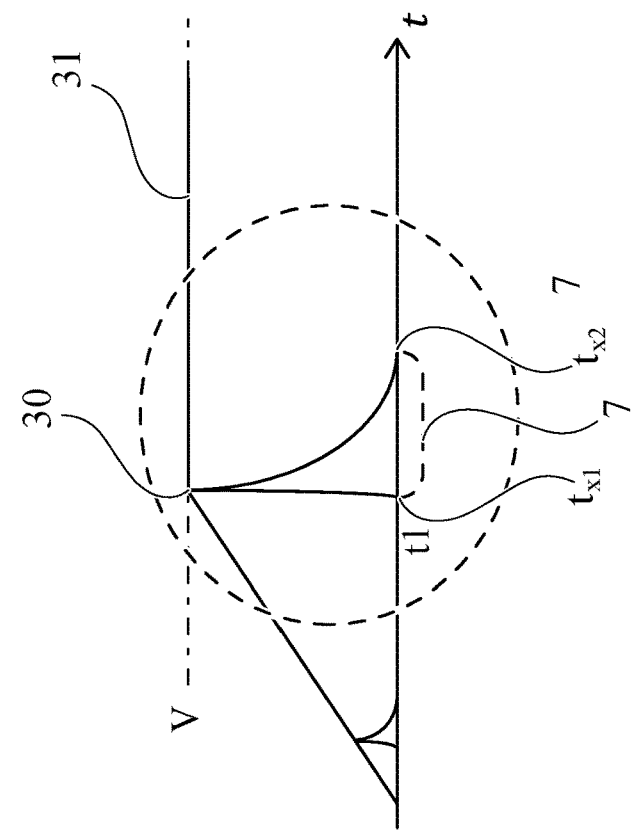
FIG. 7 shows a representation of the pulse duration of an activation signal.
Figure 7:
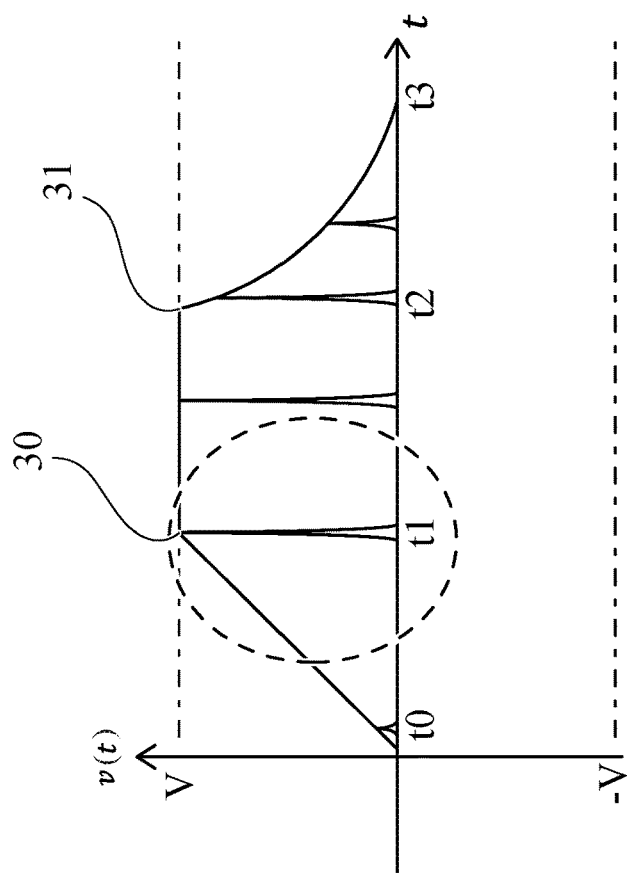

FIG. 7A is an example of an activation signal of the disclosed method in a voltage versus time diagram. Said activation signal comprises a pulsed carrier signal (30) modulated by a modulating signal (31). The modulating signal (31) is a segmented signal in three segments, from time t0 to t3, having (i) a first segment described by a positive slope ramp starting from a voltage 0 to V, (ii) a second segment from time t1 to t2, during which the modulating signal (31) limits the carrier signal (30) to a voltage equal to V, and finally, (iii) a third segment from time t2 to t3, which describes an exponential decrease in voltage that starts at a voltage V at t2 and drops to a voltage 0 at t3.

In this example, the carrier signal (30) is a series of pulses distributed in time between t0 and t3.

As can be seen in FIG. 7B, the detail of a pulse of the carrier signal (30) is shown at an instant t=t1. The pulse has a voltage amplitude equal to V and a pulse duration (7) equal to $t_{x2}$ minus $t_{x1}$. This pulse duration (7) is between 1 ns and 0.5 s. In general, the series of pulses has at least one pulse, and said series of pulses can be periodic or non-periodic.

It should be understood that when referring to the jerk generated by a magnetic field, the hysteresis of the magnetic field transducer must be considered. Typically, a magnetic field transducer has a greater hysteresis than an electric field transducer.

For this reason, in order to stimulate a tissue with jerk-generating magnetic fields, for example, an activation signal frequency is used according to the working frequency of the magnetic field transducer. In an example of the disclosed method, it is possible to obtain jerk tissue stimulation with a magnetic field transducer using a frequency ranging between 1 Hz (hertz) and 3 MHz (megahertz), and optionally between 1 Hz (hertz) and 500 kHz (kilohertz) and a pulse duration of 1 ns to 0.5 s. In another particular example, a jerk tissue stimulation is obtained with a magnetic field transducer with a frequency determined between 1 Hz (hertz) and 5 kHz (kilohertz).

Figure 2:
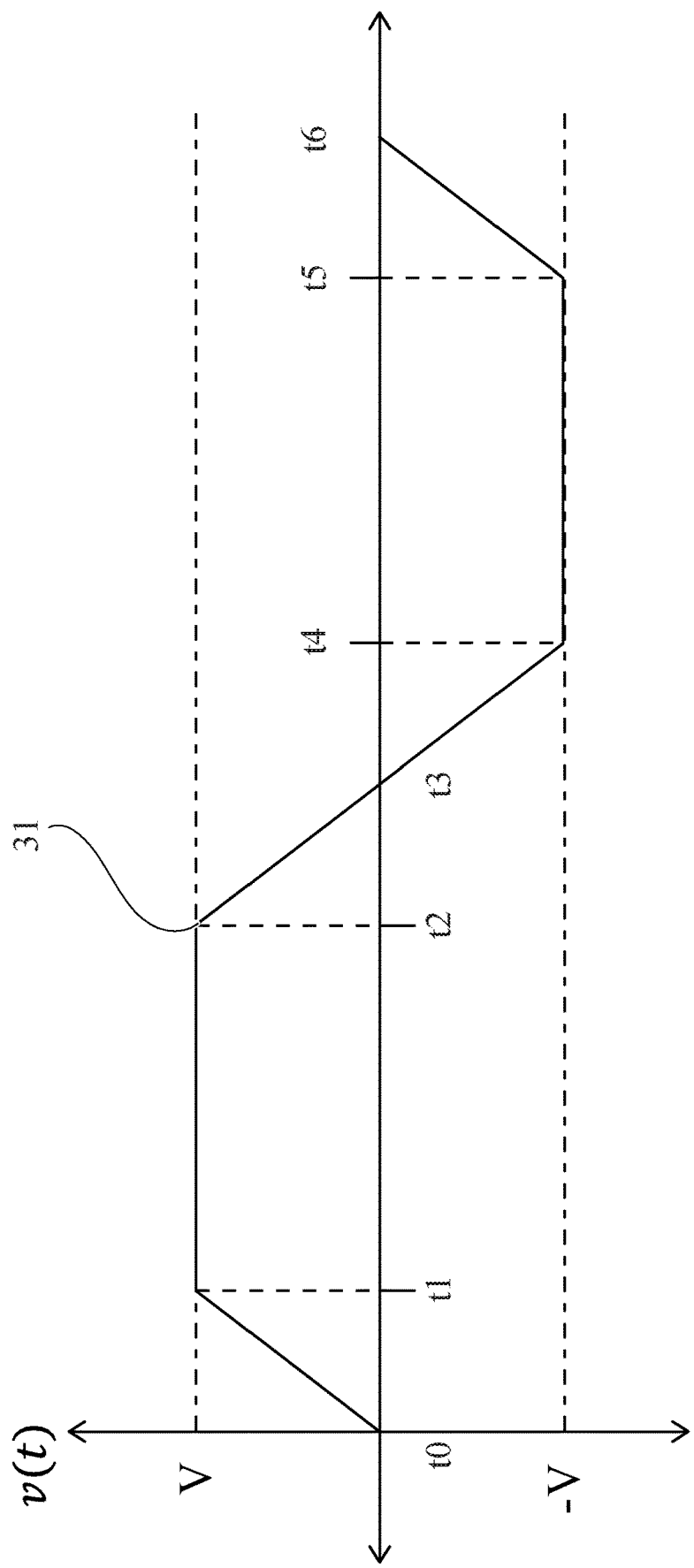
FIG. 2 shows an example of a modulating signal.

FIG. 2 shows the activation signal of an arrangement of electromagnetic transducers (electrostatic isolated transducer) in an example of the disclosed method, said activation signal (8) comprises the following six segments:

- a first segment from t0 to t1, which is a ramp-type function increasing from an initial voltage Vi to a final voltage Vf, where Vi is 0 volts and Vf is V volts;
- a second segment from t1 to t2, which is a constant voltage function V, for example, V equal to V volts;
- a third segment from t2 to t3, which is a decreasing ramp-type function from an initial voltage Vi to a final voltage Vf, where Vi equals V volts and Vf equals 0 volts;
- a fourth segment from t3 to t4, which is a decreasing ramp-type function from an initial voltage Vi to an end voltage Vf, where Vi equals 0 volts and Vf equals −V volts;
- a fifth segment from t4 to t5, which is a constant voltage function, where V equals −V volts; and
- a sixth segment from t5 to t6, which is a ramp-type function increasing from an initial voltage Vi to a final voltage Vf, where Vi is −V volts and Vf is 0 volts.

The value range that each of the variables in the example can take are listed below:

| Lower Limit | Variable | Upper limit |
|---|---|---|
| −20 kV ≤ | V | ≤ 20 kV |
| −20 kV ≤ | Vi | ≤ 20 kV |
| −20 kV ≤ | Vf | ≤ 20 kV |
| 0 ≤ | t0 | ≤ t1 |
| t0 ≤ | t1 | ≤ t2 |
| t1 ≤ | t2 | ≤ t3 |
| t2 ≤ | t3 | ≤ t4 |
| t3 ≤ | t4 | ≤ t5 |
| t4 ≤ | t5 | ≤ t6 |
| t5 ≤ | t6 | ≤ T |

Starting from said activation signal (8), different signal forms are obtained by modifying the time intervals, for example, an alternating current or direct current signal, pulsed signal, square wave signal with duty cycle variation, sawtooth wave signal, segmented signal, or combinations thereof.

The value of "t" corresponds to the period of the activation signal (8), said period being between 1 ns and 0.5 s.

Alternatively, the activation signal changes based on tissue temperature, or with a tissue impedance response feedback, or combinations of temperature feedback and tissue impedance response. Using feedback allows controlling the activation signal thus preventing tissue damage by overstimulating or accelerating tissue stimulation. For example, the above is possible either by increasing or decreasing voltage amplitude of the activation signal that is inversely proportional to tissue temperature.

Also, it is possible in step (100) to verify the activation signal that generates jerk by making successive derivatives on the activation signal up to a third derivative of said signal, in which at least one unit triplet is obtained at some point of the signal. This is described below with a particular example for a modulating signal that generates jerk.

Subsequently, step (120) consists in applying the activation signal to the arrangement of electromagnetic transducers by the computing unit; where the arrangement of electromagnetic transducers produces jerk-generating electromagnetic fields that mechanically stimulate the tissue upon application of the activation signal to the electromagnetic transducers by the computing unit.

Figure 11:
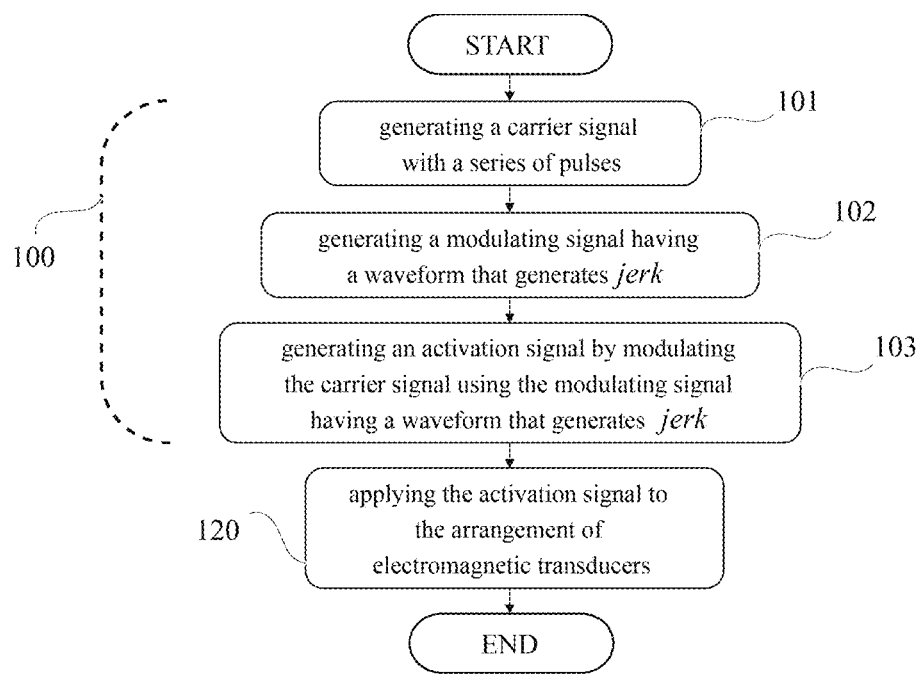
FIG. 11 shows an example of a flowchart of the method for stimulating a tissue using an arrangement of electromagnetic transducers comprising modulation of signals of this disclosure.

FIG. 11 shows an example of a flowchart of the method for stimulating a tissue using an arrangement of electromagnetic transducers comprising modulation of signals of this disclosure, the method comprises the following steps: (101) a) generating a carrier signal with a series of pulses by a signal generator; (102) b) generating a modulating signal which generates jerk by a signal generator; (103) c) generating an activation signal modulating the carrier signal with the modulating signal that generates jerk; (120) d) applying the activation signal to the arrangement of electromagnetic transducers by a computing unit; wherein the arrangement of electromagnetic transducers produces jerk-generating electromagnetic fields which mechanically stimulate the tissue upon application of the activation signal.

Figure 3:
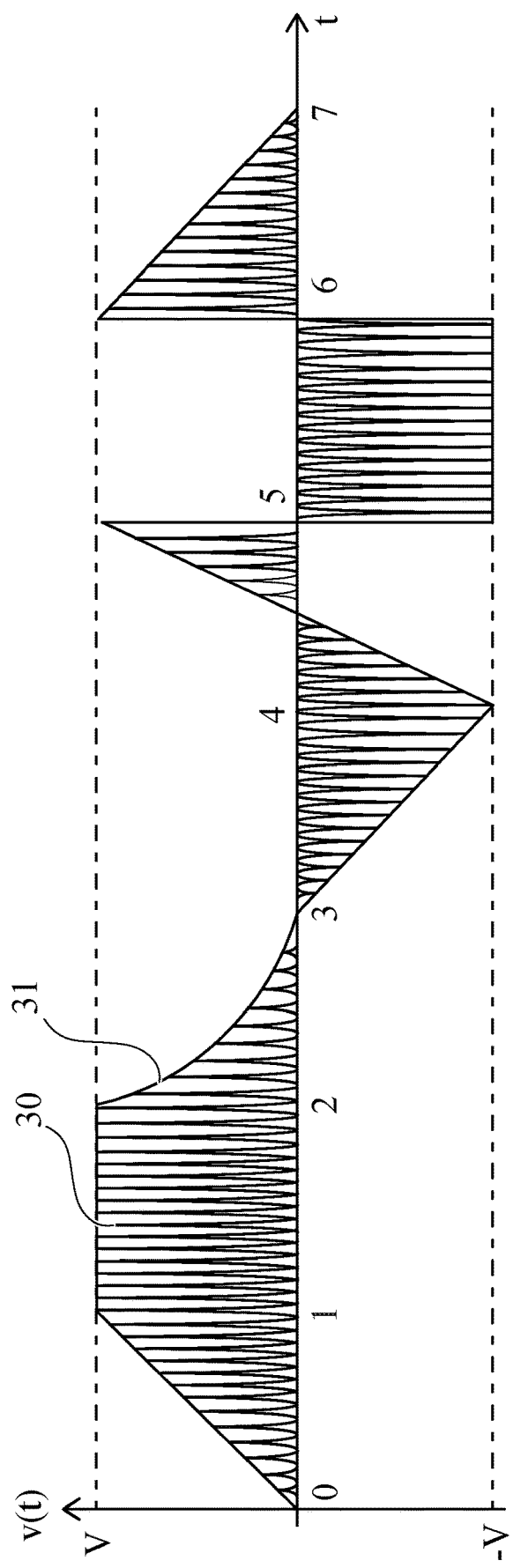
FIG. 3 shows an example of an alternate modulated and segmented signal.

Making reference to FIGS. 11 and 3, in one embodiment of the disclosed method, step (100) has the following sub-steps: (101) a) generating a carrier signal (30) with a series of pulses by a computing unit; (102) b) generating a modulating signal (31) having a waveform that generates jerk by a computing unit; (103) c) generating an activation signal by modulating the carrier signal (30) with the modulating signal having a waveform that generates jerk by a computing unit. In this way, it is possible to stimulate tissue by modifying one or more of the parameters of the activation signal such as voltage amplitude, phase, pulse duration, duty cycle or pulse position.

In sub-step (100), which consists of generating a carrier signal (30) with a series of pulses by a computing unit, said carrier signal (30) is used to stimulate the tissue of interest and also, in an example of the present disclosure, can be generated by a computing unit.

Alternatively, the carrier signal (30) is selected from a signal of alternating or non-alternating pulses, i.e. the carrier signal (30) can change its polarity alternately, thus activating the electromagnetic transducers of the arrangement of electromagnetic transducers to generate electromagnetic fields that change the electromagnetic field vector in a given time.

In an example of the disclosed method, the carrier signal (30) of alternating or non-alternating pulses is formed by a series of pulses. In an example, in sub-step (101), the series of pulses has a determined frequency between 1 Hz (hertz) and 3 MHz (megahertz). Said determined frequency may be selected by a user, but can also be programmed in the computing unit. Optionally, the series of pulses has a determined frequency between 1 Hz and 3 MHz; it is also feasible to use a frequency range between 1 Hz and 500 kHz for the tissue (3) stimulation.

In another example of the disclosed method, in sub-step (101), the carrier signal (30) is formed by a series of pulse functions having at least one pulse with a duration between 1 ns and 0.5 s.

Then, in sub-step (102) generating a modulating signal (31) with a waveform that generates jerk by a computing unit, said modulating signal (31) is used to stimulate the tissue of interest. Said modulating signal (31), found in an example of the present disclosure may be generated by a computing unit (21) or a signal generator.

The modulating signal (31) is selected between an alternating current or direct current signal, pulsed signal, squared wave signal with duty cycle variation, sawtooth wave signal, segmented signal, or combinations thereof. In an example of the disclosed method, the modulating signal (31) is a wave signal described by a segmented function with duty cycle variation.

In one embodiment, in the sub-step (102) of the disclosed method, the modulating signal (31) that generates jerk has a frequency between 0.1 Hz and 5 kHz; and, in another embodiment of the sub-step (b) the modulating signal (31) has a frequency between 0.1 Hz and 10 Hz.

In an example of the disclosed method, in the sub-step (a) the carrier signal (30) has a voltage amplitude between −20 kV and 20 kV, in the sub-step (b) the modulating signal (31) has a voltage amplitude between −20 kV and 20 kV.

Using said ranges of voltage amplitude, it is possible to obtain an intensity of the electric field in the tissue (3) between 2 V/cm and 5 V/cm when the active face of the transducers is in contact with the tissue (3) outer surface.

On the other hand, if the electric field transducers are at a defined distance from the tissue (3) outer surface then the electric field strength value is between 330 V/cm and 20 kV/cm for distances between 0.01 cm and 50 cm of the tissue (3) outer surface, and optionally between 0.01 cm and 4 cm of the tissue (3) outer surface The foregoing tries to ensure the intensity of the electric field in the tissue is between 2 V/cm and 5 V/cm.

On the other hand, if tissue stimulation is performed with magnetic field transducers, with an activation signal having a voltage amplitude between −20 kV and 20 kV it is possible to obtain a magnetic field strength that is found between 1 and 2000 Gauss.

In an example of the disclosed method, an activation signal is used with a maximum electrical voltage of 80 V applied to electric field transducers of the arrangement of electromagnetic transducers, with a distance between electrodes of 27 cm. This allows one to obtain an intensity of electric field between 3 V/cm and 5 V/cm to stimulate the tissue (3).

Moreover, in another particular example of the disclosed method, it is possible to operate at 120 V for the activation signal when the distance between electrodes is 40 cm. Said electrical voltages are applied to electrodes isolated from the tissue (3) outer surface.

The carrier signal (30) has a frequency of at least one order of frequency higher than the frequency of the modulating signal (31) However, the stimulation of the tissue (3) of interest could also be achieved even if this is not the case, for example, where the frequency of the carrier signal (30) is five times the frequency of the modulating signal (31). In a particular example, the frequency of the carrier signal (30) is ten times the frequency of the modulating signal (31).

Subsequently, sub-step (103) of the disclosed method involves the generation of an activation signal by modulating the carrier signal (30) with the modulating signal (31) that generates jerk of the sub-step (102).

Figure 4:
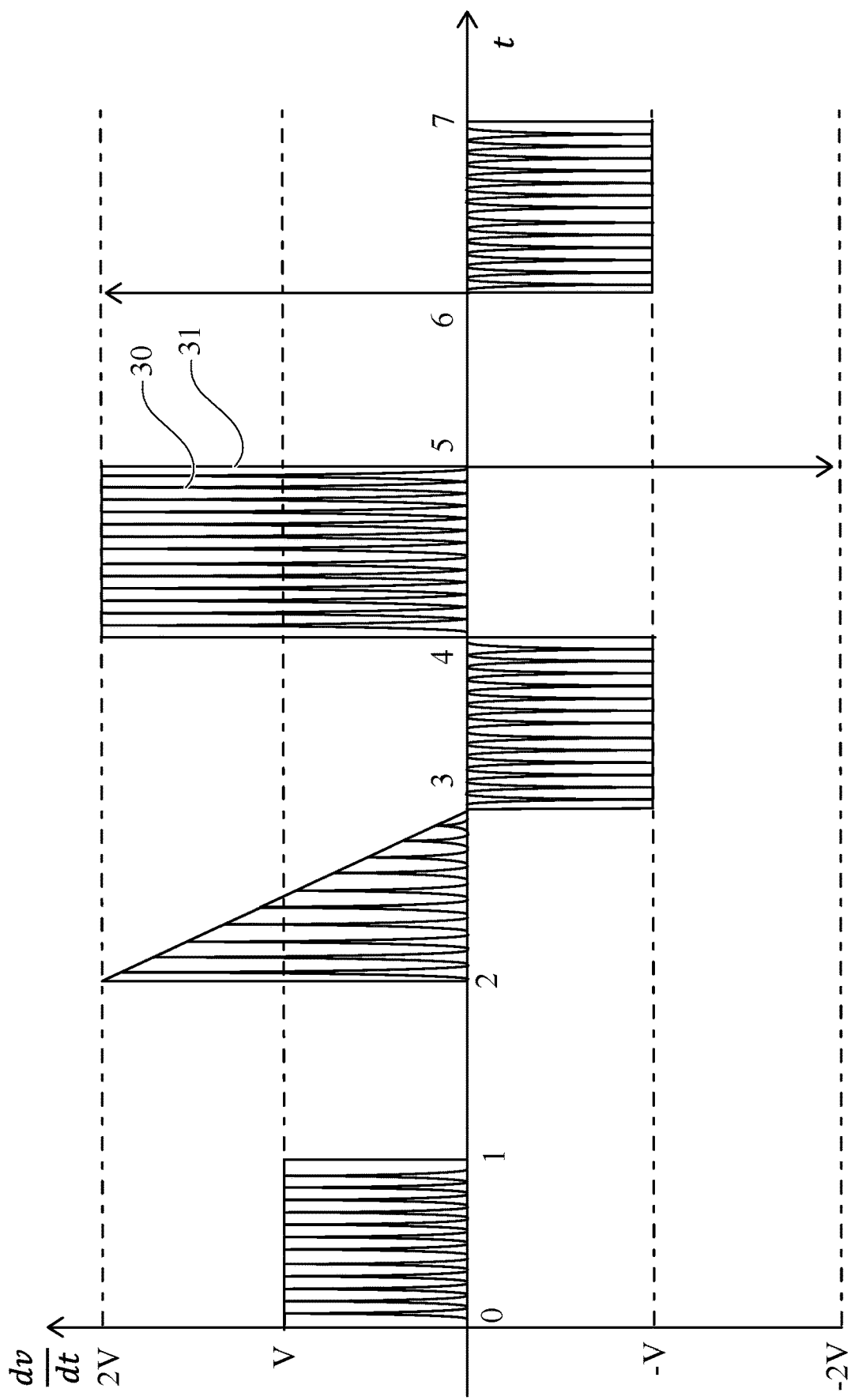
FIG. 4 shows the first derivative of the alternate modulated and segmented signal of FIG. 3.
Figure 5:
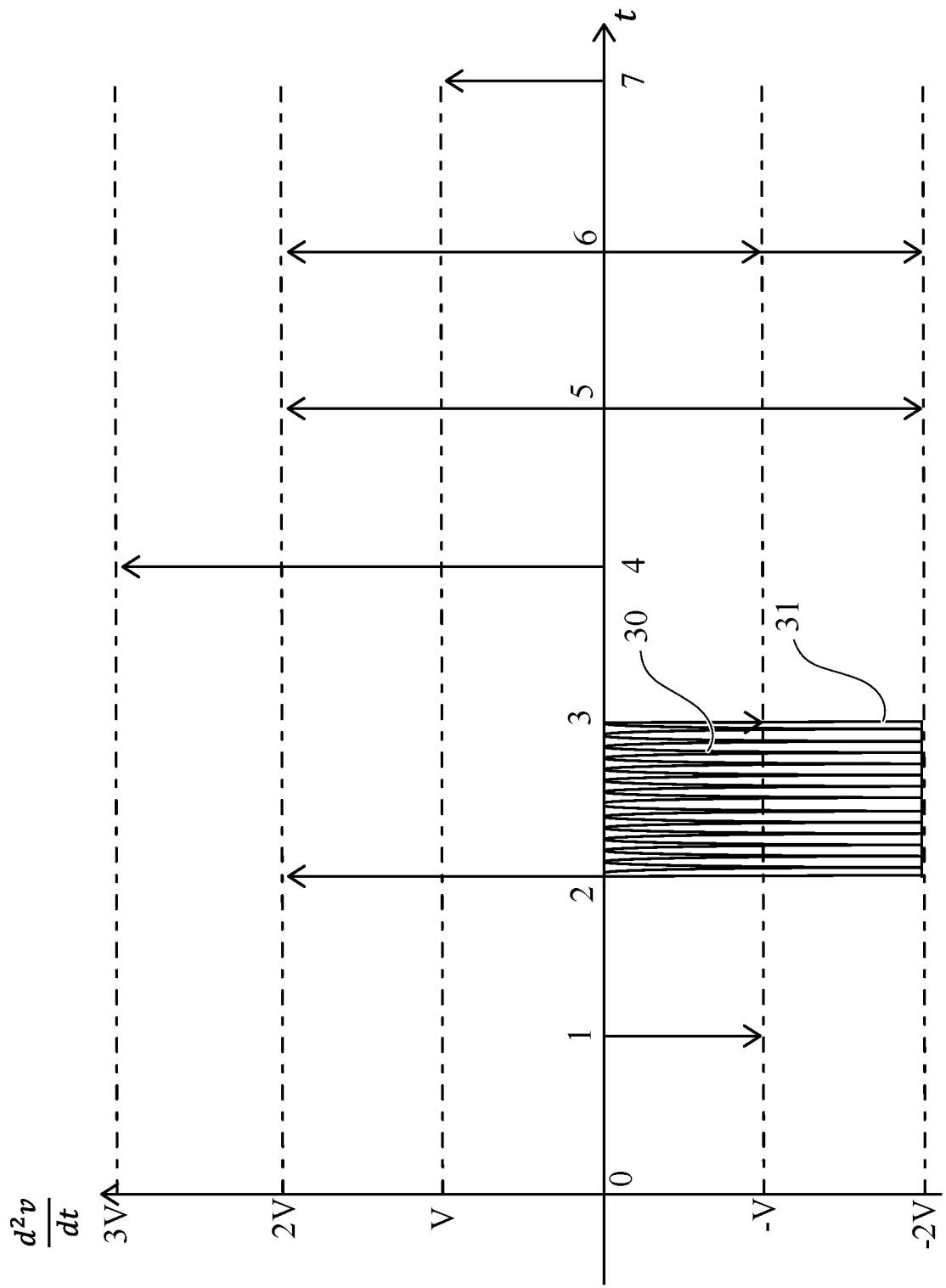
FIG. 5 shows the second derivative of the alternate modulated and segmented signal of FIG. 3.

FIGS. 3, 4 and 5 show an example of a modulated signal for an electromagnetic stimulation. Voltage (v(t)) is the differential electrical potential between the terminals of an arrangement of electromagnetic transducers (1) that varies in time (t).

Particularly, the activation signal in this example is a signal with period of seven seconds, and comprises a modulating signal (31) that generates jerk and a carrier signal (30), said modulating signal (31) is described by a segmented function comprising seven segments.

Each segment of the modulated signal has a duration of one second and a particular waveform for each section of the modulating signal (31) that follows the function by sections as described below:
  the first segment corresponds to a ramp function described by the equation $v(t)_{S01}$ equal to $(V)(t)$ from a time t 0 to 1;
  the second segment corresponds to a step function described by the equation $v(t)_{S12}$ equal to $(V)$ from a time t 1 to 2;
  the third segment corresponds to a parabolic function described by the equation $v(t)_{S23}$ equal to $-V(t-3)^2$ from a time t 2 to 3;
  the fourth segment corresponds to a ramp function described by the equation $v(t)_{S34}$ equal to $-V(t-3)$ from a time t 3 to 4;
  the fifth segment corresponds to a ramp function described by the equation $v(t)_{S45}$ equal to $2V(t-4.5)$ from a time t 4 to 5;
  the sixth segment corresponds to a step function described by the equation $v(t)_{S56}$ equal to $-V$ from a time t 5 to 6; and
  the seventh segment corresponds to a ramp function described by the equation $v(t)_{S67}$ equal to $-V(t-7)$ from a time t 6 to 7.

The carrier signal (30) has a sequence of alternate pulses with a period that may be fixed or variable in a frequency range between 1 Hz and 3 MHz, the voltage amplitude of each of the pulses of the carrier signal (30) is limited by the modulating signal (31) between −V and V, V can take any value of voltage amplitude between −20 kV and 20 kV For example, the voltage amplitude of the modulating signal (31) may be between −10 kV and 10 kV, or in another example, between −3 kV and 7 kV. That is, applying electromagnetic stimulation with electromagnetic transducers separated from the tissue at a certain distance. For example, transducers of electrostatic fields separated by a distance of 20 cm from the tissue.

In another example, in the sub-step (102) the modulating signal (31) has a voltage amplitude between −20 kV and 20 kV.

In sub-step (101), the carrier signal (30) has a frequency of at least one frequency order higher than the frequency of the modulating signal (31). For example, the modulating signal (31) has a frequency of ⅐ Hz (approximately 0.1428 Hz) and the frequency of the carrier signal (30) is between 2 Hz up to 3 kHz.

Figure 6:
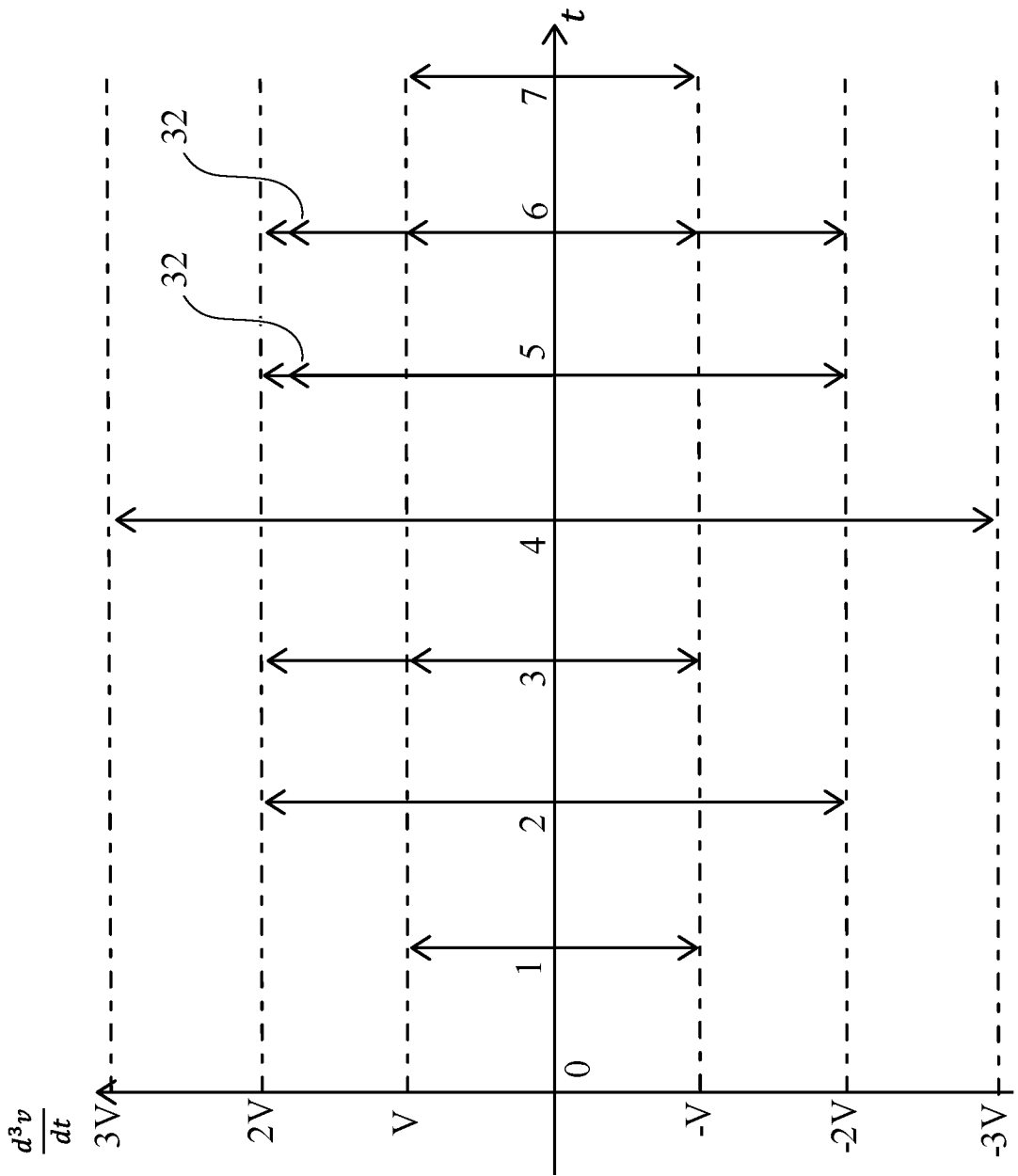
FIG. 6 shows the third derivative of the alternate modulated and segmented signal of FIG. 3.

As shown in FIG. 6, modulating signal (31) has a waveform such that a function that has at least one unit triplet (32) is obtained, when making derivatives successively up to the third derivative. In this sense, it is possible to carry out a verification of the jerk effect by making three successive derivatives of the modulating signal (31) and obtaining a unit triplet (32).

In another embodiment of the disclosed method, when the activation signal is applied to the electromagnetic transducers, the tissue responds with a variation in its parameters which are optionally measured using the same electromagnetic transducers. This measurement of the stimulated tissue acts as feedback and allows dynamically changing the features such as the frequency and pulse duration of the carrier signal (30) in sub-step 101, as well as the waveform of the modulating signal (31) in sub-step 102.

FIGS. 4, 5 and 6 describe the successive derivatives of the modulating signal (31). Particularly, FIG. 4 shows the first derivative of the modulated signal of FIG. 4. By deriving said modulating signal (31) a signal is obtained in segments, comprising seven segments as follows:
  the first segment corresponds to a step function described by the equation $$\frac{dv(t)_{S01}}{dt} = V$$

from a time t equal to U to a time t equal to 1;
  the second segment corresponds to a constant value equal to 0 from a time t equal to 1 to a time t equal to 2;
  the third segment corresponds to a ramp function described by the equation $$\frac{dv(t)_{S23}}{dt} = -2V(t-3)$$

from a time t equal to 2 to a time t equal to 3.

$$\frac{dv(t)_{S23}}{dt} = -2V(t-3)$$

from a time t equal to 2 to a time t equal to 3;
  the fourth segment corresponds to a constant value equal to −V from a time t equal to 3 to a time t equal to 4;

the fifth segment corresponds to a constant value equal to 2V from a time t equal to 4 to a time t equal to 5, additionally the derivative has a negative impulse at t equal to 5;

the sixth segment corresponds to a constant value equal to 0 from a time t equal to 5 to a time t equal to 6, additionally the derivative has a positive impulse at t equal to 6; and the seventh segment corresponds to a constant value equal to −V from a time t equal to 6 to a time t equal to 7.

In sub-step b) of step A) the modulating signal (31) is selected from an alternate current or direct current signal, pulsed signal, square wave signal with duty cycle variation, sawtooth wave signal, segmented signal, or combinations thereof, and optionally, in sub-step b) of step A) the modulation of the modulating signal (31) is selected between frequency modulation (FM), amplitude modulation (AM), phase modulation (PM), pulse width modulation (PWM), pulse position modulation (PPM), or combinations thereof.

FIG. 5 is the second derivative of the modulating signal (31) of FIG. 3 as described below:

a first segment corresponds to a constant value equal to 0 from a time t equal to 0 to a time t equal to 1 and a negative pulse at t equal to 1;

a second segment corresponds to a constant value equal to 0 from a time t equal to 1 to a time t equal to 2 and a negative pulse at t equal to 2;

a third segment corresponds to a constant value equal to −2V from a time t equal to 2 to a time t equal to 3 and a negative pulse at t equal to 3;

a fourth segment corresponds to a constant value equal to 0 from a time t equal to 3 to a time t equal to 4 and a positive pulse at t equal to 4;

a fifth segment corresponds to a constant value equal to 0 from a time t equal to 4 to a time t equal to 5 and a negative unit doublet at t equal to 5;

a sixth segment corresponds to a constant value equal to 0 from a time t equal to 5 to a time t equal to 6 and a positive unit doublet at t equal to 6; and a seventh segment corresponds to a constant value equal to 0 from a time t equal to 6 to a time t equal to 7 and a positive pulse at t equal to 7.

FIG. 6 is the third derivative of the modulating signal (31) of the example of FIG. 3. This figure has the following segments:

a first segment corresponds to a constant value equal to 0 from a time t equal to 0 to a time t equal to 1 and a negative unit doublet at t equal to 1;

a second segment corresponds to a constant value equal to 0 from a time t equal to 1 to a time t equal to 2 and a negative unit doublet at t equal to 2;

a third segment corresponds to a constant value equal to 0 from a time t equal to 2 to a time t equal to 3, a negative pulse and another positive pulse at t equal to 3;

a fourth segment corresponds to a constant value equal to 0 from a time t equal to 3 to a time t equal to 4 and a positive unit doublet at t equal to 4;

a fifth segment corresponds to a constant value equal to 0 from a time t equal to 4 to a time t equal to 5 and a negative unit triplet at t equal to 5;

a sixth segment corresponds to a constant value equal to 0 from a time t equal to 5 to a time t equal to 6 and a positive unit triplet at t equal to 6; and a seventh segment corresponds to a constant value equal to 0 from a time t equal to 6 to a time t equal to 7 and a positive unit doublet at t equal to 7.

It is to be understood that, the unit triplet is theoretically the second derivative of an impulse function, which is a mathematical representation of jerk for the purpose of the present disclosure and it corresponds to the rate of change or variation of the acceleration in the vector of the electromagnetic, electrostatic, electric or magnetic field.

Below is a table with a summary of the functions results illustrated in FIGS. 3, FIG. 4 and FIG. 5:

| Equation | $D^1$ | $D^2$ | $D^3$ |
|---|---|---|---|
| $v(t)_{S01} = (V)(t)$ | $\dfrac{dv(t)_{S01}}{dt} = V$ | 0 | 0 |
| $v(t)_{S12} = (V)$ | 0 | 0 | 0 |
| $v(t)_{S23} = -V(t-3)^2$ | $\dfrac{dv(t)_{S23}}{dt} = -2V(t-3)$ | $\dfrac{d^2 v(t)_{S23}}{dt} = -2V$ | 0 |
| $v(t)_{S34} = -V(t-3)$ | $\dfrac{dv(t)_{S34}}{dt} = -V$ | 0 | 0 |
| $v(t)_{S45} = 2V(t-4.5)$ | $\dfrac{dv(t)_{S45}}{dt} = 2V$ | 0 | 0 |
| $v(t)_{S56} = -V$ | 0 | 0 | 0 |
| $v(t)_{S67} = -V(t-7)$ | $\dfrac{dv(t)_S}{dt} = -V$ | 0 | 0 |

Finally, in an example of the disclosed method, step (120) consists in applying the activation signal to the arrangement of electromagnetic transducers (1) by a computing unit (21). This activation signal has a waveform with at least one jerk per period, which allows the tissue (3) to be stimulated with disruptive changes of electromagnetic fields applied on a tissue (3).

In another embodiment, the disclosed method comprises the following steps: AA) generating a carrier signal (30) with a series of pulses, each pulse with a duration between 1 ns (nanoseconds) and 0.5 s (seconds), a voltage between −20 kV (kilovolts) and 20 kV (kilovolts) and a frequency between 1 Hz (hertz) and 3 MHz (megahertz); BB) generating a modulating signal (31) that produces jerk which is the change in the acceleration of tissue cells by the generated electromagnetic field, said modulating signal (31) with a voltage between −20 kV (kilovolts) and 20 kV (kilovolts) and a frequency between 0.1 Hz (hertz) and 5 kHz (kilohertz); CC) generating an activation signal modulating the carrier signal (30) with the modulating signal (31) that produces jerk; and DD) applying the activation signal to an arrangement of electromagnetic transducers (1); wherein electromagnetic fields generated mechanically stimulate the tissue, upon application of the activation signal to the electromagnetic transducers by the computing unit (21).

Alternatively, in an embodiment of the device for stimulating a tissue with electromagnetic fields (11) comprises a computing unit (21), an external power source (22) connected to the computing unit (21), a decoupling circuit (23) connected to the external power source (22), and an arrangement of electromagnetic transducers (1) connected to the computing unit (21), the arrangement of electromagnetic transducers (1) is functionally disposed over the tissue (3); wherein the computing unit (21) is configured to: A) generate an activation signal having a waveform that generates electromagnetic field jerk by a computing unit (21); and B) apply the activation signal to the arrangement of electromagnetic transducers (1) by the computing unit (21);

wherein the arrangement of electromagnetic transducers (1) produces jerk-generating electromagnetic fields which mechanically stimulate the tissue (3) upon application of the activation signal.

In another embodiment, during step A) of the implemented method the following sub-steps are executed: a) generating a carrier signal with a series of pulses by a computing unit; b) generating a modulating signal having a waveform that generates jerk by a computing unit; c) generating an activation signal by modulating the carrier signal using the modulating signal having a waveform that generates jerk by a computing unit.

Alternatively, in an embodiment of the device for stimulating a tissue with electromagnetic fields (11), the device (11) comprises a computing unit (21); an external power source (22) connected to the computing unit (21); a decoupling circuit (23) connected to the external power source (22) and to the computing unit (21); and an arrangement of electromagnetic transducers (1) connected to the computing unit (21), the arrangement is functionally disposed over the tissue (3); wherein the computing unit (21) is configured to: AA) generate a carrier signal (30) with a series of pulses by a computing unit (21); BB) generate a modulating signal (31) that produces jerk by a computing unit (21); CC) generate an activation signal by modulating the carrier signal (30) using the modulating signal (31) that produces jerk by a computing unit (21); DD) apply the activation signal to the arrangement of electromagnetic transducers (1) by a computing unit (21); wherein the arrangement of electromagnetic transducers (1) produces jerk-generating electromagnetic fields which mechanically stimulate the tissue upon application of the activation signal.

Optionally, in an embodiment of the device for stimulating a tissue with electromagnetic fields (11) the arrangement of electromagnetic transducers (1) is connected to the computing unit (21), thus allowing the computing unit (21) to directly manage the activation signal applied upon the arrangement of electromagnetic transducers (1).

Devices for stimulating a tissue with electromagnetic fields (11) can be used to reduce the particle size of a material.

Example of the Use of a Method and a Device of the Disclosure Applied in an Individual Having Deep Tissue Melanomas:

The following tissue stimulation was carried out in conjunction with Tissue-stimulating method using frequency scanning of electric and magnetic fields as described in international application No. PCT/IB2019/051007 and application Tissue-stimulating method using spatial scanning of electric and magnetic fields as described in international application No. PCT/IB2019/051005.

A tissue stimulation was performed in an individual with the following initial findings:

Two deep tissue melanomas, each one of them located in each individual forearm and three deep tissue melanomas located in the ventral surface of the chest, the melanomas having a straight circular cone shape with a base diameter of 2 cm.

The procedure for stimulating said deep tissue melanomas in the said individual was the following:

An arrangement of 10 electromagnetic transducers was located around the deep tissues melanomas locations, then a carrier signal with a series of pulses having a fixed frequency of 15.75 kHz with a duty cycle of 0.8% and a voltage of 400 Vpp (Peak-to-Peak Voltage) was generated by a computing unit, then a modulating square wave signal with a frequency variation between 150 Hz and 350 Hz with a duty cycle of 50% and a voltage of 400 Vpp was generated. After said square wave signal was generated, the modulating signal with the carrier signal was modulated to obtain the activation signal, next, the activation signal was applied to the arrangement of electromagnetic transducers by the computing unit thus mechanically stimulating the tissue upon application of the activation signal.

The tissue stimulation described below was carried out in conjunction with the method described in international application No. PCT/IB2019/051007. As such, the results provided below are the result of the combination of these two methods.

The individual received the above-described stimulation for a six hours period of time thus finally achieving a reduction of approximately 50% of the size of the deep tissue melanomas was observed in the individual.

Example of a Material Particle Size Reduction Using a Method of the Disclosure with a Disclosed Device:

Commercial grade granular native corn starch (Maizena) Unilever Andina Colombia Ltda., Cali, Colombia, was acquired in the local trade. Ten grams of native corn starch sample was weighted. The maximum particle size of native corn starch sample is expected to be approximately 308 μm according to NTC 926 (available in https://tienda.icontec.org/wp-content/uploads/pdfs/NTC926.pdf) as US Tyler No. 60 and No. 80 sieves are used to outline the particle size of native corn starch national regulations (available in https://www.icbf.gov.co/sites/default/files/ftp-fecula de maiz-150224.pdf) and the standard specification for woven wire test sieve cloth and test sieves ASTM e 11-09 (available in http://sieve.advantechmfg.com/Asset/ASTM%20E%2011-13% 20Standards%20Table.pdf).

A pair of square shape parallel plates electrodes measuring 2 cm×2 cm was located around the native corn starch sample, both parallel plates located at a distance of 5 cm from the sample, then a carrier signal with a series of pulses having a fixed frequency of 6 kHz with a duty cycle of 30% and a voltage of 4 kVpp (Peak-to-Peak kilovolts) was generated by a computing unit, then a modulating square wave signal with a fixed frequency of 25 Hz with a duty cycle of 50% and a voltage of 4 kVpp was generated. After said square wave signal was generated, the modulating signal with the carrier signal was modulated to obtain the activation signal, next, the activation signal was applied to the arrangement of electromagnetic transducers by the computing unit thus mechanically reducing the particle size of the native corn starch sample upon application of the activation signal.

After applying the described electric stimulation to the sample finer grain size was obtained.

DEFINITIONS AND ACRONYMS

AM Amplitude Modulation
AMOLED Active Matrix Organic Light Emitting Diode
ASIC Application Specific Integrated Circuits
CPLD Complex Programmable Logic Devices
DSC Digital Signal Controllers
EEG Electroencephalogram.
EMF Electromagnetic Fields.
FM Frequency Modulation
FPGA Field Programmable Gate Arrays
HID Human Interface Device
LCD Liquid Crystal Display
LED Light Emitting Diode
OLED Organic Light Emitting Diode
PEMF Pulsed Electromagnetic Fields.

PM Phase Modulation
PPM Pulse Position Modulation
PSoC Programmable Systems on Chip
PWM Pulse Width Modulation
QD Quantum Display
SoC Systems on Chip The present disclosure is not limited to the embodiments described and illustrated. It will be evident to a person skilled in the art that there are variations and possible modifications that do not depart from the spirit of the disclosure, which is only defined by the following claims.

The invention claimed is:

1. A method for stimulating a tissue using an arrangement of electromagnetic transducers, the method comprising the following steps:
   A) generating an activation signal having a waveform that generates electromagnetic field jerk by a computing unit; and
   B) applying the activation signal to the arrangement of electromagnetic transducers by the computing unit;
   wherein the arrangement of electromagnetic transducers produces jerk-generating electromagnetic fields capable of stimulating the tissue upon application of the activation signal;
   wherein said waveform is described by a mathematical function wherein at least a unit triplet is obtained in its third derivative at some point of the mathematical function.

2. The method of claim 1, wherein the electromagnetic transducers of the arrangement of electromagnetic transducers are selected from electrical field transducers, magnetic field transducers, electrostatic field transducers, and combinations thereof.

3. The method of claim 2, wherein the electromagnetic transducers are selected from electrical field transducers and the electrostatic field transducers are selected from the group consisting of motors, electrodes, photoelectric transducers, electric induction actuators, conductive plates that generate electric fields, antennas, and combinations thereof.

4. The method of claim 2, wherein the electromagnetic transducers are selected from magnetic field transducers selected from the group consisting of motors, magnetic induction actuators, core or non-core coils that generate magnetic fields, electromagnets, antennas and combinations thereof.

5. The method of claim 1, wherein in step A) the activation signal is selected from the group consisting of an alternating current or direct current signal, a pulsed signal, a squared wave signal with variation of duty cycle, a triangular wave signal, a sawtooth wave signal, a segmented signal, and combinations thereof.

6. The method of claim 1, wherein in step A), the activation signal is an alternating or non-alternating pulse signal.

7. The method of claim 1, wherein in step A), the computing unit changes the following parameters: voltage amplitude, frequency and phase, based on a tissue temperature feedback.

8. The method of claim 1, wherein in step A), the computing unit changes the following parameters: voltage amplitude, frequency and phase, based on a tissue impedance response feedback.

9. The method of claim 1, wherein step A) has the following sub-steps:
   a) generating a carrier signal with a series of pulses by the computing unit;
   b) generating a modulating signal having the waveform that generates the jerk by the computing unit; and
   c) generating the activation signal by modulating the carrier signal using the modulating signal having the waveform that generates the jerk by the computing unit.

10. The method of claim 9, wherein in sub-step a), the carrier signal is a signal of alternating pulses.

11. The method of claim 9, wherein in sub-step a), the carrier signal has a frequency of at least one frequency order greater than the frequency of the modulating signal.

12. The method of claim 9, wherein in sub-step a), the carrier signal formed by the series of pulses has at least one pulse with a duration between about 1 ns and about 0.5 s.

13. The method of claim 9, wherein in sub-step b), the modulating signal is selected from the group consisting of an alternating current signal, a direct current signal, a pulsed signal, a squared wave signal with variation of a duty cycle, a triangular wave signal, a sawtooth wave signal, a segmented signal, and combinations thereof.

14. The method of claim 9, wherein in sub-step c), the modulation of the carrier signal is selected from the group consisting of: frequency modulation (FM), amplitude modulation (AM), phase modulation (PM), pulse width modulation (PWM), pulse position modulation (PPM), and combinations thereof.

15. The method of claim 9, wherein the computing unit changes the modulating signal and the carrier signal based on a tissue temperature feedback.

16. The method of claim 9, wherein the computing unit changes the modulating signal and the carrier signal based on a tissue impedance response feedback.

17. A method for stimulating a tissue by an arrangement of electromagnetic transducers comprising the following steps:
   a) generating a carrier signal with a series of pulses by a computing unit;
   b) generating a modulating signal that generates jerk by the computing unit;
   c) generating an activation signal by modulating the carrier signal using the modulating signal that generates jerk by the computing unit; and
   d) applying the activation signal to the arrangement of electromagnetic transducers by the computing unit;
   wherein the arrangement of electromagnetic transducers produces jerk-generating electromagnetic fields capable of stimulating tissue upon application of the activation signal;
   wherein the activation signal has a waveform described by a mathematical function wherein at least a unit triplet is obtained in its third derivative at some point of the mathematical function.

18. The method of claim 17, wherein in step a), the carrier signal with a series of pulses is a signal of alternating pulses or non-alternating pulses.

19. The method of claim 17, wherein in step a), the carrier signal has a frequency of at least one frequency order greater than the frequency of the modulating signal.

20. The method of claim 17, wherein in step a), the carrier signal with a series of pulses has at least one pulse with a duration between about 1 ns and about 0.5 s.

21. The method of claim 17, wherein in step b), the modulating signal is selected from the group consisting of an alternating current signal, a direct current signal, a pulsed signal, a squared wave signal with variation of the duty cycle, a triangular wave signal, a sawtooth wave signal, a segmented signal, and combinations thereof.

22. The method of claim 17, wherein in step c), the modulation of the carrier signal is selected from the group consisting of modulation by variation of voltage amplitude, modulation by phase variation, modulation by variation of duty cycle, modulation by variation of pulse position, and combinations thereof.

23. The method of claim 17, wherein the computing unit changes the voltage amplitude, frequency and phase parameters of the modulating signal and the carrier signal, based on a tissue temperature feedback.

24. The method of claim 17, wherein the computing unit changes the voltage amplitude, frequency and phase parameters of the modulating signal and the carrier signal, based on a tissue impedance response feedback.

25. The method of claim 1 or 17, for the use in reducing a particle size of a material.

26. A device for stimulating a tissue with electromagnetic fields, the device comprising:
a computing unit;
an external power source connected to the computing unit;
a decoupling circuit connected to the external power source and to the computing unit; and
an arrangement of electromagnetic transducers connected to the computing unit and to the decoupling circuit, wherein the arrangement of electromagnetic transducers is configured to be disposed over the tissue;
wherein the computing unit is configured to:
A) generate an activation signal having a waveform that generates an electromagnetic field that generates jerk; and
B) apply the activation signal to the arrangement of electromagnetic transducers;
wherein the arrangement of electromagnetic transducers produces jerk-generating electromagnetic fields capable of stimulating the tissue, upon application of the activation signal;
wherein said waveform is described by a mathematical function wherein at least a unit triplet is obtained in its third derivative at some point of the mathematical function.

27. The device of claim 26, wherein the computing unit is configured to:
a) generate a carrier signal with a series of pulses;
b) generate a modulating signal having the waveform that generates jerk; and
c) generate the activation signal by modulating the carrier signal using the modulating signal having a waveform that generates jerk.

28. The device of claim 26, for use in reducing a particle size of a material.

29. The device of claim 26, for use in reducing a particle size of the tissue.

30. A device for stimulating a tissue with electromagnetic fields,
the device comprising:
a computing unit;
an external power source connected to the computing unit;
a decoupling circuit connected to the external power source and to the computing unit; and
an arrangement of electromagnetic transducers connected to the computing unit and to the decoupling circuit, wherein the arrangement of electromagnetic transducers is configured to be disposed over the tissue;
wherein the computing unit is configured to:
a) generate a carrier signal with a series of pulses;
b) generate a modulating signal that generates jerk;
c) generate an activation signal by modulating the carrier signal using the modulating signal that generates jerk; and
d) apply the activation signal to the arrangement of electromagnetic transducers;
wherein the arrangement of electromagnetic transducers produces jerk-generating electromagnetic fields capable of stimulating the tissue, upon application of the activation signal;
wherein the activation signal has a waveform described by a mathematical function wherein at least a unit triplet is obtained in its third derivative at some point of the mathematical function.

* * * * *